United States Patent [19]

Turner

[11] Patent Number: 4,533,381

[45] Date of Patent: Aug. 6, 1985

[54] NAPHTHYRIDINYLOXY(OR THIO)PHENOXY PROPANOIC ACIDS, DERIVATIVES THEREOF AND METHODS OF HERBICIDAL USE

[75] Inventor: James A. Turner, Pittsburg, Calif.

[73] Assignee: The Dow Chemical Company, Midland, Mich.

[21] Appl. No.: 651,556

[22] Filed: Sep. 17, 1984

Related U.S. Application Data

[62] Division of Ser. No. 395,415, Jul. 6, 1982, Pat. No. 4,472,193.

[51] Int. Cl.³ .................... C07D 487/04; A01N 43/40
[52] U.S. Cl. .......................................... 71/94; 546/122; 546/123
[58] Field of Search ........................ 546/122, 123, 157; 71/94

[56] References Cited

U.S. PATENT DOCUMENTS

| | | | |
|---|---|---|---|
| 4,105,435 | 8/1978 | Nishiyama et al. | 71/94 |
| 4,236,912 | 12/1980 | Johnston | 71/94 |
| 4,401,459 | 8/1983 | Samtoni et al. | 71/94 |
| 4,447,259 | 5/1984 | Ohyama et al. | 71/94 |
| 4,448,966 | 5/1984 | Lee | 546/302 |
| 4,472,193 | 9/1984 | Turner | 71/94 |
| 4,477,276 | 10/1984 | Unkel et al. | 71/94 |
| 4,479,001 | 10/1984 | Johnston et al. | 546/291 |
| 4,491,468 | 1/1985 | Johnston | 71/94 |

Primary Examiner—Henry R. Jiles
Assistant Examiner—Barbara C. Cassatt
Attorney, Agent, or Firm—S. Preston Jones; Ronald G. Brookens

[57] ABSTRACT

Novel 2-naphthyridinyloxy(or thio)phenoxy propanoic acid compounds of the formula

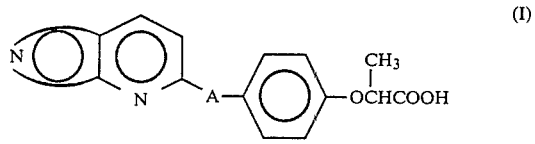

(I)

wherein

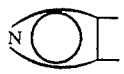

represents a 6 membered nitrogen containing an aromatic ring which forms a 1,5-, 1,6-, 1,7- or 1,8-naphthyridinyl moiety with the adjoining pyridine ring, said naphthyridinyl moiety optionally substituted at the 6 position of the naphthyridinyl moiety with a chloro, bromo, iodo, $CF_3$, or fluoro atom;

A represents 0 or S; and agriculturally acceptable salts, esters, ethers, and amides thereof, are useful as fungicides and herbicides, particularly effective against grassy weeds.

17 Claims, No Drawings

NAPHTHYRIDINYLOXY(OR THIO)PHENOXY PROPANOIC ACIDS, DERIVATIVES THEREOF AND METHODS OF HERBICIDAL USE

CROSS-REFERENCE TO RELATED APPLICATION

This is a divisional of application Ser. No. 395,415, filed July 6, 1982, now U.S. Pat. No. 4,472,193.

BACKGROUND OF THE INVENTION

The present invention relates to novel 2-(naphthyridinyloxy(or thio)phenoxy)propanoic acids and agriculturally acceptable salts, amides, ethers and esters thereof, optionally substituted in the 6 position of the naphthyridine ring system. The present invention also relates to herbicidal and fungicidal compositions of such novel compounds and methods of using such compounds for the control of grassy weeds and fungi.

Various aryloxy(or thio)phenoxy alkanoic acids are known as herbicides. U.S. Pat. No. 4,236,912 discloses quinolinyloxy(or thio)phenoxy alkanoic acids and derivatives thereof. European Patent Application No. 483, published Feb. 7, 1979, discloses 2-pyridyloxy(or thio)-phenoxy alkanoic acids and derivatives thereof. Belgian Pat. No. 834,495, issued Feb. 2, 1976, as well as the published German patent application equivalent thereto, viz., No. 2,546,251, published Mar. 29, 1976, describe 2-((4-pyridinyl-2-oxy)phenoxy)alkanoic acids, salts and esters having a halo substitution in the 3 and-/or 5 ring positions in the pyridine ring. Published Japanese Patent Application No. 129,313/75, filed in Japan on Oct. 29, 1975 teaches pyridyloxyphenoxypropanols and esters thereof, while published Japanese Patent Application No. 064,160/75, filed on May 30, 1975, teaches pyridyloxyphenoxypropionitrile compounds.

Heretofore, naphthyridinyloxy(or thio)phenoxy propanoic acids and agriculturally acceptable salts, amides, ethers and esters thereof have not been disclosed.

SUMMARY OF THE INVENTION

The present invention is directed to 2-naphthyridinyloxy(or thio)phenoxy propanoic acids corresponding to the formula

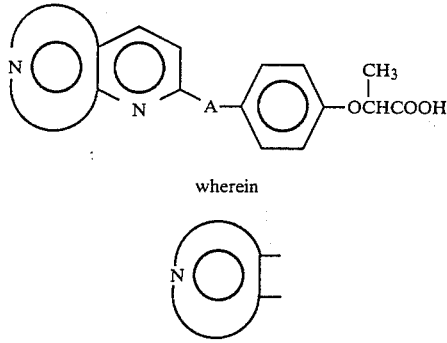

wherein

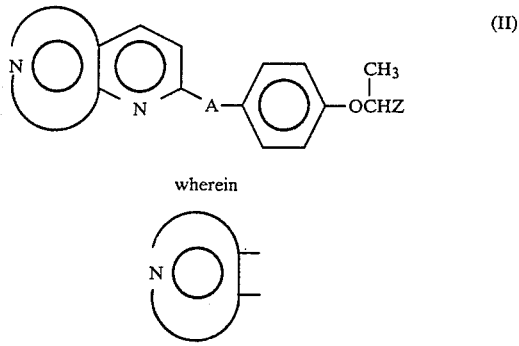

represents a six-membered nitrogen-containing aromatic ring which when fused to the above shown pyridyl ring forms a 1,5-, 1,6-, 1,7- or 1,8- naphthyridinyl moiety optionally substituted at the 6 position of the naphthyridinyl moiety with a chloro, iodo, $CF_3$, bromo, or fluoro atom with the proviso that said substitution occurs only when the 6-position of said naphthyridinyl moiety is occupied by a carbon atom;

A represents O or S; and agriculturally acceptable salts, amides, ethers, and esters thereof.

The compounds of the above Formula I, hereinafter referred to as "active ingredients", have been found to be active as herbicides and fungicides. Accordingly, the present invention also encompasses compositions containing one or more active ingredients as well as methods of controlling unwanted vegetation and fungi. Such methods comprise, for example, applying a herbicidally effective amount of one or more active ingredients preemergently or post-emergently to the locus of the undesired vegetation, and particularly to the locus where a valuable crop is to germinate and grow.

DETAILED DESCRIPTION

The term "herbicide" is used herein to mean an active ingredient which controls or adversely modifies the growth of plants. By "growth controlling" or "herbicidally-effective" amount is meant an amount of active ingredient which causes an adversely modifying effect and includes deviations from natural development, killing, regulation, dessication, retardation, and the like. The term "plants" is meant to include germinant seeds, emerging seedlings and established vegetation.

The term "plants", when used herein, is meant to include germinant seeds, emerging seedlings, as well as established vegetation.

The term "agriculturally acceptable salts, amides, ethers and esters", when used to describe the active ingredients disclosed herein, is meant to encompass any salt, amide, ether or ester of said active ingredients (acids) which does not substantially affect the herbicidal activity of said active ingredients. Agriculturally acceptable salts, amides, ethers and esters of the active ingredients include compounds of the formula and A are as hereinbefore defined;

Z represents $—CO_2H$ (the acids), $—CO_2M$, $—CO_2R$, $—COSR$, $—CONR'_2$, $—CSNH_2$, $—CN$, $—CH_2OR'$ or $—CH_2O_2CR'$;

M represents Na, K, Mg, Ca or $N(R'')_4$;

R represents $C_1–C_8$ alkyl or $C_3–C_6$ alkoxyalkyl;

each R' independently represents H or $C_1–C_4$ alkyl; and

R" independently represents H, $C_1–C_4$ alkyl or $C_2–C_3$ hydroxyalkyl.

The terms "$C_1–C_4$ alkyl" and "$C_1–C_8$ alkyl" refer to different size alkyl groups which may be straight, branched, or cyclic, when the group contains at least three carbon atoms, and, contain 1–4 or 1–8 carbon atoms respectively.

The terms "$C_2–C_3$ hydroxyalkyl" and "$C_3–C_6$ hydroxyalkyl" refer to different size hydroxyalkyl groups having 2–3 or 3–6 carbon atoms, respectively, and the alkyl portion may be straight or branched, or cyclic when the group contains at least three carbon atoms.

The active ingredients of the present invention are generally crystalline solids at ambient temperatures which are generally soluble in many organic solvents commonly employed as herbicidal carriers such as alcohols, acetone, chloroform, aromatic petroleum solvents and methylene chloride.

Active ingredients within the scope of the present invention include 2-(1,5-naphthyridinyl) oxy(or thio)-phenoxy propanoic acids; 2-(1,6-naphthyridinyl)oxy(or thio)phenoxy propanoic acids; 2-(1,7-naphthyridinyl)oxy(or thio)phenoxy propanoic acids; 2-(1,8-naphthyridinyl)oxy(or thio)phenoxy propanoic acids and agriculturally acceptable salts, amides, ethers and esters thereof. These active ingredients include compounds represented by the following formulas:

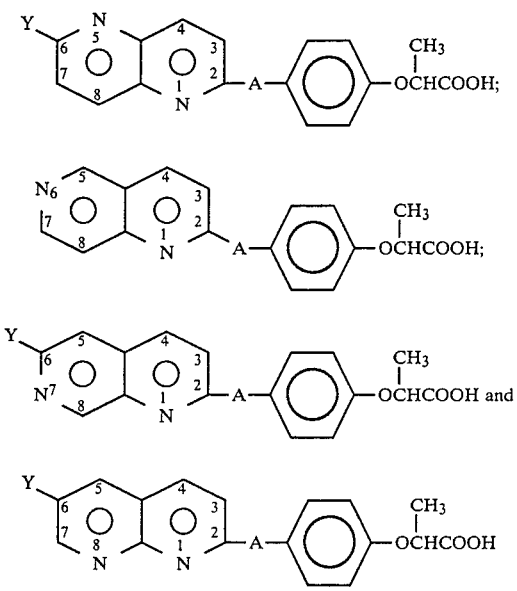

wherein

Y represents H, Cl, I, CF₃, Br or F, and A represents O or S.

The active ingredient of the above Formula I which is 2-(4-((6-chloro-2-(1,5-naphthyridinyl))oxy)phenoxy)-propanoic acid and its agriculturally acceptable salts, amides, ethers, and esters constitute preferred compounds of the present invention.

The 2-naphthyridinyloxyphenoxy propanoic acids are prepared by reacting an appropriately substituted 2-halonaphthyridine with the disodium or dipotassium salt of 2-(4-hydroxyphenoxy)propanoic acid in a suitable solvent medium, such as, dimethylsulfoxide (DMSO), dimethylformamide (DMF), hexamethyl-pyrophosphoramide or tetrahydrofuran (THF). Alternatively a monosodium or monopotassium salt of 2-(4-hydroxyphenoxy)propanoic acid alkyl ester is reacted with an appropriately substituted 2-halonaphthyridine to form the alkyl ester derivative. The reaction is advantageously carried out at a temperature in the range of from about 60° C. to about 150° C. and preferably from about 75° C. to about 110° C. under ambient atmospheric pressure.

The 2-naphthyridinylthiophenoxy propanoic acids are prepared by reacting an appropriately substituted 2-halonaphthyridine with 2-(4-mercaptophenoxy)-propanoic acid in a suitable solvent medium, such as, DMSO, DMF, hexamethylpyrophosphoramide or THF. The reaction is advantageously carried out at a temperature in the range of from about 60° C. to about 150° C. and preferably from about 75° C. to about 110° C. under ambient atmospheric pressure.

The reaction between the naphthyridine and the hydroxy- or mercapto-phenoxy propanoic acid starting materials is carried out in a polar solvent such as, DMSO, to which has been added about 2 molar equivalents of a base such as sodium hydroxide or potassium carbonate. The reaction is usually carried out at a temperature in the range of from about 70° to about 150° C. and usually the reaction is complete in about ½ to about 8 hours. The pressure at which the reaction is carried out is not critical and the reaction is generally conducted at ambient atmospheric pressure. After the reaction is substantially complete, the reaction mixture is allowed to cool to room temperature and then poured into cold water and thereafter acidified by the addition of HCl. The desired product, i.e. naphthyridinyloxy (or thio)phenoxy propanoic acid compound, is then extracted and purified, employing known extraction and purification techniques, such as, for example extraction with methylene chloride and thereafter evaporating the methylene chloride under vacuum resulting in a solid or an oil which is then triturated with water to give a solid product.

Once the naphthyridinyloxy(or thio)phenoxy propanoic acid compounds of the present invention are prepared, the agriculturally acceptable salts, amides, ethers and esters thereof, hereinbefoe described, are readily made in accordance with well known procedures relating to the preparation of salts, amides, ethers and esters of propanoic acid and substituted propanoic acid compounds. U.S. Pat. No. 4,236,912, which discloses the preparation of quinolinyloxy(or thio)phenoxy alkanoic acids and derivatives thereof, describes methods analogous to those employed in making the agriculturally acceptable salts, amides, ethers and esters of the active ingredients and is hereby incorporated by reference and made a part hereof.

The following examples illustrate the present invention and the manner in which it can be practiced but, as such, are not to be construed as limitations upon the overall scope of the same.

EXAMPLE 1

Preparation of 2-(4-((6-chloro-2-(1,5-naphthyridinyl))oxy)phenoxy)-propanoic acid

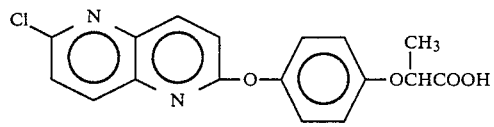

To a stirred, nitrogen flushed mixture of 270 mg (1.5 mmoles) of 2-(4-hydroxy)phenoxy propanoic acid and 420 mg (3 mmoles) of powdered anhydrous potassium carbonate in 15 ml of DMSO was added 300 mg (1.5 mmoles) of 2,6-dichloro-1,5-naphthyridine. The mixture was slowly warmed to 105°–110° C. and maintained at this temperature range for one hour. The mixture was cooled to room temperature, poured into water and then extracted with methylene chloride. The aqueous layer was then made acidic by the addition of 6N HCl and then extracted twice with methylene chloride. The methylene chloride phases were then combined, washed twice with water and then evaporated to dryness under vacuum. The resulting oil was triturated with water to give an off-white solid. The solid was recrystallized once from toluene/pentane and once from toluene/hexane to give 327 mg of white crystals having a melting point of 139°–143° C. Upon analysis, the prepared compound exhibited a carbon, hydrogen and nitrogen content of 58.67, 3.84 and 7.76 percent, respectively, as compared to the theoretical contents of 59.22, 3.80 and 8.13 percent, respectively, calculated for $C_{17}H_{13}ClN_2O_4$.

EXAMPLE 2

Preparation of 2-(4-(1,8-naphthyridin-2-yloxy)phenoxy)propanoic acid

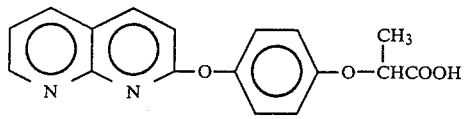

A 3-necked flask was equipped with a thermometer, a magnetic stirrer, a reflux condenser and a nitrogen line and flushed with nitrogen. The flask was charged with 15 ml of hexane and 1.38 gm (28.8 mmoles) of 50% NaH/oil dispersion. After stirring for 10 minutes the hexane was decanted and replaced with 5 ml of DMSO followed by the dropwise addition of a solution of 2.18 gm (12 mmoles) of 2-(4-hydroxyphenoxy)propanoic acid in 5 ml of DMSO. The mixture was warmed to 60° C. and a solution of 1.97 gm of 2-chloro-1,8-naphthyridine in 10 ml of DMSO was added. After warming the reaction mixture at 95° C. for one hour, the mixture was cooled to room temperature and water cautiously added. The solution was extracted with methylene chloride and the aqueous phase neutralized with acetic acid to give a white precipitate. The aqueous mixture was extracted with $CH_2Cl_2$ and the organic layer washed twice with water, dried over $Na_2SO_4$ and evaporated to dryness to give 3.3 gm of yellow solid which could not be redissolved in ether or $CH_2Cl_2$.

EXAMPLE 3

Preparation of 2-(4-(2-(1,8-naphthyridinyl)oxy)phenoxy)propanic acid, methyl ester

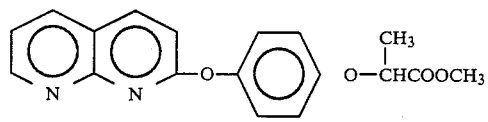

Thionyl chloride (15 ml) was added to 3.1 gm of 2-(4-(1,8-naphthyridin-2-oxy)phenoxy)propanic acid and this solution was heated at reflux for 3 hours. After cooling, the solution was diluted with 25 ml of toluene. The solvent was then removed by vacuum distillation. The residual solid was diluted with 50 ml of toluene and then 5 ml of methanol was slowly added. After 3 hours of stirring at room temperature, the mixture was poured into water and the aqueous layer made basic with NaOH. The aqueous layer was then extracted twice with $CH_2Cl_2$. The combined organic layers were then washed twice with water, dried over $Na_2SO_4$ and evaporated to dryness. The residue was purified by silica gel chromatography, eluting with 50% ethyl acetate/hexane, to give a brown gum (0.5 gm) which was pure by thin layer chromatography (TLC) and nuclear magnetic resonance (NMR) criteria. Carbon, hydrogen and nitrogen content by weight percent calculated for $C_{18}H_{16}N_2O_4$ is C, 66.85; H, 4.97; N, 8.64; which compared to that actually found of C, 65.41; H, 5.06; and N, 8.43.

EXAMPLE 4

Preparation of 2-(4-(2-(1,6-Naphthyridinyl)oxy)phenoxy)propanoic acid, methyl ester

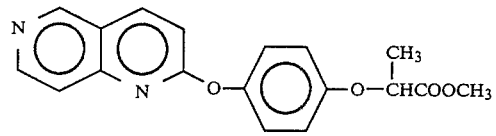

A nitrogen flushed flask was charged with 1.18 gm (6 mmoles) of 2-(4-hydroxyphenoxy)propanoic acid, methyl ester, 20 ml of dry DMSO, 0.99 gm (7.2 mmoles) of dry powdered potassium carbonate and 0.99 gm (6 mmoles) of 2-chloro-1,6-naphthyridine. This mixture was warmed at 80° C. for one hour. After cooling to room temperature the mixture was poured into water and extracted 3 times with ether. The combined ether layers were washed with 5% aqueous NaOH, dried over $MgSO_4$ and evaporated to dryness. The residual solid was recrystallized from methylcyclohexane to give 1.58 gm (81%) of the product as white platelets having a melting point of 88°–90° C. Carbon, hydrogen and nitrogen analysis calculated for $C_{18}H_{16}N_2O_4$ is C, 66.65; H, 4.97; N, 8.64, which compares to that actually found of C, 66.41; H, 4.99; and N, 8.60.

EXAMPLE 5

Preparation of 2-(4-((6-chloro-2-(1,7-naphthyridinyl))oxy)phenoxy)-propanoic acid, methyl ester

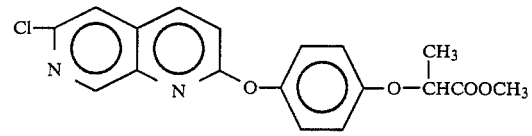

Step 1: Preparation of 2,2-dimethyl-N—(2-chloro-5-pyridinyl)propanamide

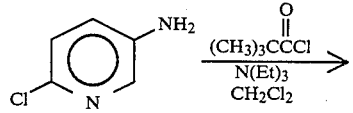

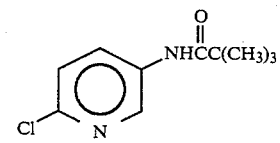

To an ice-cooled solution of 45 g (0.35 mole) of 5-amino-2-chloropyridine and 42.4 g (0.42 mole) of triethylamine in 300 ml of $CH_2Cl_2$ was added, dropwise, a solution of 44.3 g (0.368 moles) of trimethyl acetyl chloride in 60 ml of dichloromethane over a period of 1.5 hours. This mixture was stirred at room temperature for 2 hours, poured into 5% aqueous NaOH and the dichloromethane layer separated. The organic layer was washed with 5% aqueous NaOH, dried over $Na_2SO_4$ and evaporated to leave a brown oil which solidified on standing. This solid was taken up in hot ethyl acetate, treated with charcoal, filtered and diluted with hexane. Cooling this solution resulted in the precipitation of 58.7 g (79% of theoretical) of white crystals having a melting point of 120°–123° C. Carbon, hydrogen and nitrogen content calculated for $C_{10}H_{13}ClN_2O$ is C, 56.47; H, 6.16; and N, 13.17 percent by weight which compared to that actually found of C, 56.31; H, 6.14; and N, 13.02 percent by weight.

Step 2: Preparation of 2,2-dimethyl-N-(2-chloro-4-formyl-5-pyridinyl)propanamide

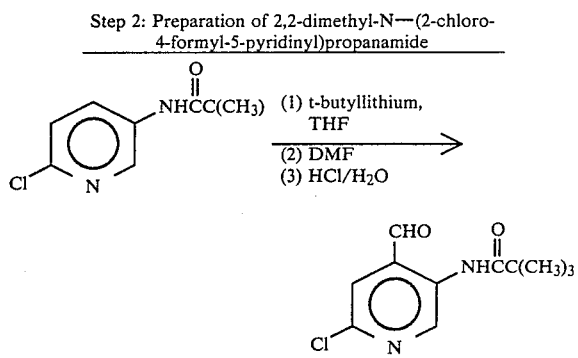

A three-necked flask, equipped with a thermometer, a magnetic stirrer and a nitrogen inlet, was flushed with nitrogen. The flask was charged with 10.63 g of 2,2-dimethyl-N-(2-chloro-5-pyridinyl)propanamide (50 mmoles) and stoppered with a rubber septum. 100 Ml of THF was added to the flask. The flask was cooled in a liquid $N_2$/MeOH slush bath and 52.4 ml (110 mmoles) of 2.1M t-butyllithium was slowly added maintaining the temperature $\leq 75°$ C. by the rate of addition. The flask was transferred to a dry-ice/isopropanol (IPA) bath and stirred for 1.5 hours when a solution of 10.95 g (150 mmoles) of dimethylformamide in 5 ml of THF was added. The mixture was stirred at −78° C. for 30 minutes, 40 ml of 6N HCl was then added to the flask and the reaction mixture was allowed to warm to room temperature. After stirring for 30 minutes at room temperature, water and ether were added and the organic layer was separated. The aqueous layer was washed twice with ether and the combined organic layers washed with saturated NaCl, dried over $MgSO_4$ and evaporated to leave an oil. The oil was triturated sequentially with water and ether and filtered to remove precipitated solids. The ethereal filtrate was recovered and dried over $MgSO_4$ and the ether evaporated. Chromatography of the oil residue by preparative liquid chromatography (eluting with 20% EtOAc (ethyl acetate)/hexane) gave 3.5 g of the aldehyde (29% of theoretical) as a pale yellow solid. The solid was recrystallized from hexane to give yellow needles having a melting point of 105°–106.5° C. Carbon, hydrogen, nitrogen and chlorine content calculated for $C_{11}H_{13}ClN_2O$ is C, 54.89; H, 5.44; N, 11.64 and Cl, 14.73 percent by weight which compares to that actually found upon analysis of C, 54.79; H, 5.38; N, 11.63; and Cl, 14.74.

Step 3: Preparation of 2-chloro-3-((2,2-dimethyl-1-oxopropyl)amino)-β-hydroxy-4-pyridine propanoic acid, 1,1-dimethyl ethyl ester

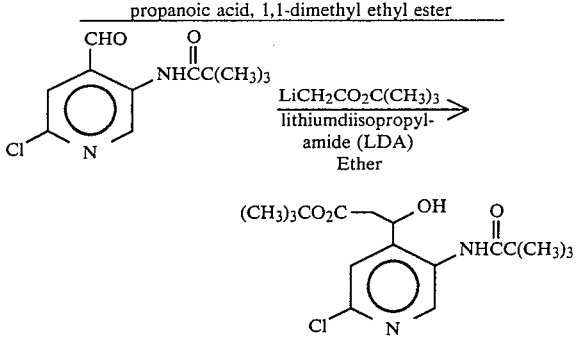

An oven-dried, 3-necked flask, equipped with a magnetic stirrer, a thermometer and a nitrogen inlet, was flushed with nitrogen. The flask was stoppered with a rubber septum and charged with 100 ml of ether and 7.9 ml (56.7 mmoles) of diisopropylamine. The solution was cooled in a dry-ice/IPA bath while 34.3 ml (56.7 mmoles) of 1.65M n-butyllithium in hexane was added. After stirring at −78° C. for 15 minutes, a solution of 3.45 g (29.7 mmoles) of t-butylacetate in 5 ml of ether was slowly added. After 15 minutes a solution of 6.5 g (27 mmoles) of 2,2-dimethyl-N-(2-chloro-4-formyl-5-pyridinyl)propanamide in 20 ml of ether and 5 ml of THF was slowly added to immediately give a yellow precipitate. The reaction mixture was stirred at −78° C. for 15 minutes, slowly warmed to room temperature and poured into water. The ether layer was separated and the aqueous phase extracted twice with ether. The combined organic layers were washed with saturated NaCl, dried over $MgSO_4$ and evaporated to dryness. The residual gum was purified by preparative liquid chromatography eluting with 30% ethyl acetate/hexane. After removal of solvent, the resulting gum was taken up in hot hexane containing a trace of acetone. Upon cooling, 6.24 g (65% of theoretical) of white crystals of the above-captioned compound formed having a melting point of 123°–125° C. The carbon, hydrogen, nitrogen and chlorine content calculated for $C_{17}H_{25}ClN_2O_4$ is C, 57.21; H, 7.06; N, 7.85; and Cl, 9.94 percent by weight which compares to that actually found upon analysis of C, 56.91; H, 7.03; N, 7.83; and Cl, 10.19.

Step 4: Preparation of 6-chloro-1,7-naphthyridine-2-one

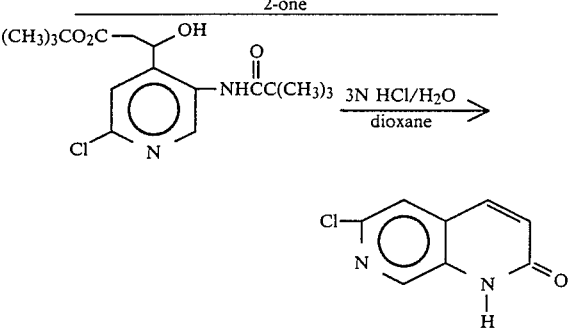

A solution of 4.63 g (13 mmoles) of 2-chloro-5-((2,2-dimethyl-1-oxopropyl)amino)-β-hydroxy-4-pyridine propanoic acid, 1,1-dimethylethyl ester in 70 ml of dioxane and 30 ml of 3N HCl in water was warmed at reflux for a period of 4 hours. The solution was diluted with 100 ml of water and cooled to give a white precipitate. The crystals were filtered, washed with water and dried in a vacuum oven to give 2.18 g (93% of theoretical) of the above-captioned compound having a melting point of 304°-306° C. The carbon, hydrogen and nitrogen content calculated for $C_8H_5ClN_2O$ is C, 53.20; H, 2.79; and N, 15.52 percent by weight which compares to that actually found upon analysis of C, 53.55; H, 2.79; and N, 15.47.

Step 5: Preparation of 2,6-dichloro-1,7-naphthyridine

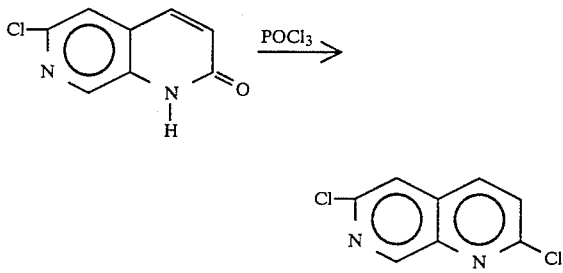

A mixture of 1.08 g (6 mmoles) of 6-chloro-1,7-naphthyridin-2-one and 10 ml of $POCl_3$ were warmed at reflux for one hour to give a clear solution. Upon cooling, a precipitate formed and the mixture was poured cautiously over ice. $CH_2Cl_2$ was added and the mixture was neutralized with solid $K_2CO_3$. The $CH_2Cl_2$ layer was separated and the aqueous layer washed twice with $CHCl_3$. The combined organic layers were washed with water, dried over $K_2CO_3$ and evaporated to give a white solid. The solid was recrystallized from hexane/acetone to give 1.14 g (95% of theoretical) of the desired product as short, white needles having a melting point of 213°-216° C. Analysis calculated for $C_8H_4Cl_2N_2$: C, 48.27; H, 2.03; N, 14.08. Found: C, 48.80; H, 2.09; N, 14.55.

Step 6: Preparation of 2-(4-((6-chloro-2-(1,7-naphthyridinyl))oxy)phenoxy) propanoic acid, methyl ester

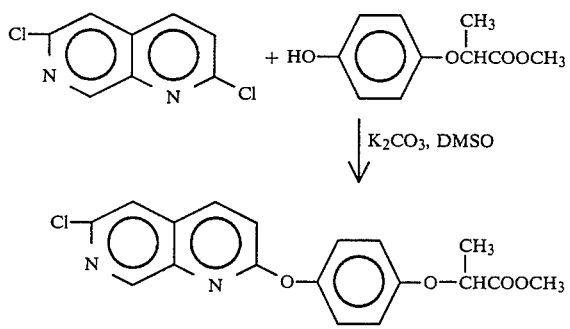

An oven-dried, three-necked flask, equipped with a thermometer, a magnetic stirrer and a reflux condenser attached to a nitrogen inlet, was flushed with nitrogen. The flask was charged with 0.83 g (6 mmoles) of anhydrous powdered $K_2CO_3$, 1.08 g (5.5 mmoles) of 2-(4-hydroxyphenoxy)propanoic acid, methyl ester, 1 g (5 mmoles) of 2,6-dichlor-1,7-naphthyridine and 20 ml of DMSO. The mixture was warmed with an oil bath at 80°-85° C. for 1.5 hours, cooled to room temperature and poured into 2% aqueous NaOH. The mixture was extracted three times with ether and the combined organic layers were washed twice with water, dried over $MgSO_4$ and evaporated to dryness to give a white solid. The solid was recrystallized from methylcyclohexane to give 1.57 g (88% of theoretical) of white crystals having a melting point of 126°-128° C. Analysis calculated for $C_{18}H_{15}ClN_2O_4$: C, 60.25; H, 4.21; N, 7.81. Found: C, 60.11; H, 4.16; N, 7.70.

The compounds of the present invention have been found to be suitable for use in methods for the pre-emergent and post-emergent control of grasses, such as, barnyard grass, crabgrass, yellow foxtail and johnson grass, in the presence of broadleaf crops, such as, cotton, soybeans and sugar beets.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

Organic solvents that can be employed include toluene, xylene, kerosene, diesel fuel, fuel oil, and petroleum naphtha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients of the present invention can also be applied as aerosols, e.g., by dispersing them by means of a compressed gas such as one of the hydrocarbon successors to the fluorocarbons which are shortly to be banned.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products e.g., Pluronic 61 (molecular weight about 1000), polyethylene glycol ester of tall oil acids, sodium octophenoxyethoxyethyl sulfate, tris(polyoxyethylene)sorbitan monostearate (Tween 60), and sodium dihexylsulfosuccinate.

The concentration of the active ingredients in solid or liquid compositions generally is from about 0.003 to about 95 percent by weight or more. Concentrations from about 0.05 to about 50 percent by weight are often employed. In compositions to be employed as concentrates, the active ingredient can be present in a concentration from about 5 to about 98 weight percent, preferably 15-50 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power dusters, boom and hand sprayers, spray dusters, by addition to irrigation water, and by other conventional means. The compositions can also be applied from airplanes as a dust or spray since the active ingredients are effective at very low application rates.

The active ingredients of the present invention have been found to possess desirable herbicidal activity in general against grassy weeds such as foxtail, barnyard grass and crabgrass in pre-emergent operations and also against the same grasses in post-emergent operations. The active ingredients possess desirable herbicidal activity against the grassy weeds, described above, while at the same time are tolerant or selective to broadleaf crops such as cotton, soybeans and sugar beets.

The exact rate to be applied is dependent not only on a specific active ingredient being applied, but also on a particular action desired (e.g., general or selective control), the plant species to be modified and the stage of growth thereof as well as the part of the plant to be contacted with the toxic active ingredient. Thus, it is to be understood that all of the active ingredients of the present invention and compositions containing the same may not be equally effective at similar concentrations or against the same plant species. In non-selective pre-emergence and foliar treatments, the active ingredients of the invention are usually applied at an approximate rate of from about 0.5 to about 5 pounds/acre, but higher rates may be appropriate in some cases such as 20 pounds/acre or more. In pre-emergent operations for selective uses a dosage of about 0.01 to about 10 pounds/acre or more is generally applicable, a rate of 0.05 to 4 pounds/acre being preferred and about 0.1 to about 2 pounds/acre being most preferred. For controlling an infestation of annuals, a dosage of about 0.1 to 0.5 pound/acre is generally utilized. When the infestation consists largely of perennials, a dosage of from 0.1 to 4, preferably 0.5 to 2.0 pounds/acre should be employed.

In post-emergent operations a dosage of about 0.01 to about 20 pounds/acre or more is generally applicable, although not all compounds are equally effective and some weeds are more difficult to control. A dosage rate in the range of about 0.05 to about 0.75 pounds/acre is preferred in selective post-emergent control of annual grassy weeds, while about 0.5 to about 5 pounds/acre is preferred and more preferably about 0.5 to about 2 pounds/acre for the selective post-emergent control of perennial grassy weeds.

EXAMPLE 6

Representative compositions of the present invention were evaluated for the post-emergence control of species of plants listed in Table A. In these evaluations, plots of the plant species listed in Table A, grown to a height of about 4 inches, were used. Aqueous spray compositions, containing various amounts of 2-(4-((6-chloro-2-(1,5-naphthyridinyl))-oxy)phenoxy)propanoic acid, i.e., 250 ppm, 125 ppm, 62.5 ppm, 31.25 ppm, 15.6 ppm and 7.8 ppm, respectively, were applied to separate plots. The spray compositions were made by mixing the active ingredient and an emulsifier or dispersant with about 1:1 water/acetone solution to provide spray compositions containing the aforementioned concentrations of active ingredient. The application to the plants was made to the point of run-off (250 ppm provides approximately 0.625 lb active ingredient per acre) and was carried out with conventional spraying equipment. Other plots were sprayed with similar compositions containing no toxicant to serve as controls. Thereafter, the plots were maintained under conditions conductive for plant growth. Two weeks after treatment, the plots were examined for plant growth and evaluated on a scale of 0 to 100 where 0 represents no effect and 100 represents complete kill. The results of the examination of the treated plots are set forth below in Table A.

TABLE A

Percent Kill and Control of Plants at Various Concentrations (ppm) of 2-(4-((6-chloro-2-(1,5-naphthyridinyl))oxy)phenoxy)propanoic acid

| Plant | Control | 250 | 125 | 62.5 | 31.25 | 15.6 | 7.8 |
|---|---|---|---|---|---|---|---|
| Corn | 0 | 90 | 80 | 50 | 20 | 0 | —* |
| Rice | 0 | 50 | 50 | 60 | 30 | 15 | 0 |
| Sorghum | 0 | 60 | 75 | 60 | 70 | 65 | 15 |
| Wheat | 0 | 50 | 80 | 40 | 10 | 20 | 0 |
| Barnyard Grass | 0 | 100 | 95 | 80 | 55 | 15 | 0 |
| Crabgrass | 0 | 95 | 95 | 95 | 90 | 75 | 30 |
| Yellow Foxtail | 0 | 95 | 100 | 95 | 60 | 0 | — |
| Johnson | 0 | 100 | 95 | 95 | 95 | 75 | 40 |

TABLE A-continued

| | Percent Kill and Control of Plants at Various Concentrations (ppm) of 2-(4-((6-chloro-2-(1,5-naphthyridinyl))oxy)phenoxy)propanoic acid | | | | | | |
|---|---|---|---|---|---|---|---|
| Plant | Control | 250 | 125 | 62.5 | 31.25 | 15.6 | 7.8 |
| Grass Wild Oats | 0 | 40 | 10 | 0 | — | — | — |

*"—" denotes not tested

At 250 ppm 2-(4-((6-chloro-2-(1,5-naphthyridinyl))-oxy)phenoxy)propanoic acid was inactive against cotton, rape, soybeans, sugar beets, jimson weed, morning glory, pigweed, velvet leaf and cockleburr.

When employing substantially the same procedure as that described in Example 5, 2-(4-((6-chloro-2-(1,7-naphthyridinyl))oxy)phenoxy)propanoic acid, methyl ester, at a concentration of 2,000 ppm (approximately 5 lbs/acre) completely killed sugar beets and barnyard grass and reduced the growth by 95 percent in johnson grass, 99 percent in corn, 90 percent in crabgrass, 70 percent in wheat and 50 percent in sorghum.

In a representative operation, 2-(4-((6-chloro-2-(1,5-naphthyridinyl)oxy)phenoxy)propanoic acid to be utilized in a series of tests is dissolved in acetone to one half of the final volume (twice the final concentration) to be used and the acetone solution in each case is admixed with an equal volume of water containing 0.1 percent by weight of Tween-20 surface active material (Tween-20 is a trademark of Atlas Chemical Company). The composition, generally in the nature of an emulsion, was employed to treat separate respective seed beds of sandy loam soil of good nutrient content wherein each seed bed contained separate groups of good viable seeds, each group being of one of a known plant species. The various beds were positioned side by side and exposed to substantially identical conditions of temperature and light. Each bed was maintained so as to prevent any interaction with the test compound in different seed beds. Each seed bed was treated with the composition as a soil drench applied at one of two predetermined rates to deposit a predetermined amount of the compound uniformly throughout the surface of the bed. Another seed bed was treated only with the acetone-Tween-20 water mixture with no chemical added to serve as a control. After treatment, the seed beds were maintained for two weeks under greenhouse condition conductive for good plant growth and watered as necessary. The specific plant species, dosage and the percent preemergent control obtained are set forth in Table 8 below. Control refers to the reduction in growth of the test species in the presence of the test chemical relative to the observed growth of the same species in the absence of the test chemical.

TABLE B

| | Premergence Control of Plant Species (%) Exhibited by 2-(4-((6-Chloro-2-(1,5-naphthyridinyl)oxy)phenoxy)propanoic Acid | | | | | | | | |
|---|---|---|---|---|---|---|---|---|---|
| | Plant Species | | | | | | | | |
| Dosage in Lbs. Per Acre | Corn | Rice | Sorghum | Wheat | Barnyard Grass | Crab Grass | Johnson Grass | Wild Oats | Yellow Foxtail |
| 2 | 75 | 100 | 100 | 100 | 100 | 80 | 100 | 70 | 100 |
| 1 | 70 | 100 | 90 | 80 | 100 | 100 | 100 | 40 | 100 |
| 0.5 | 70 | 60 | 20 | 20 | 10 | 70 | 80 | 0 | 40 |
| 0.25 | 35 | 20 | 0 | 0 | 0 | 0 | 10 | —[a] | 0 |

[a]"—" denotes not tested

The compounds of the present invention have also been found to exhibit antifungal properties. For example, 2-(4-(1,8-naphthyridinyl)oxy)phenoxy propanoic acid, when employed as the sole toxicant in a standard fungicide screening test at a concentration of 500 ppm by weight of the total composition, was shown to kill and control 90% of the grape downey mildew organisms. When 2-(4-(2-(1,6-naphthyridinyl)oxy)phenoxy)-propanoic acid, methyl ester was employed as the sole toxicant in a standard fungicide screening test at a concentration of 25 ppm by weight of the total composition, 90% of tobacco black shank pathogen Phytophthora parasitica var. Nicotianeae were controlled.

For all such fungicidal uses, unmodified active ingredients of the present invention can be employed. However, the present invention embraces the use of a fungicidally-effective amount of the active ingredients in composition form with an inert nonphytotoxic material known in the art as an adjuvant or carrier in solid or liquid form.

The compounds of the present invention contain an optically active center as shown in Formula (I) (2 position of the propanoic acid) and can exist in optically active stereoisomeric forms such as the dextrorotatory and levorotatory forms of each of the above configurations. The various mixtures and racemates of the above isomers are within the scope of the present invention.

In further embodiments, the compounds of the present invention or compositions containing the same, can be advantageously employed in combination with one or more additional pesticidal compounds. Such additional pesticidal compounds may be insecticides, nematocides, arthropodicides, herbicides, fungicides or bactercides that are compatible with the compounds of the present invention in the medium selected for application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from 1 to 100 parts of the compound of the present invention with from 100 to 1 parts of the additional compound(s).

Starting Materials

The halonaphthyridine starting materials, described herein, are prepared by employing procedures disclosed in Y. Hamada and I. Takeuchi, *Chem. Pharm. Bull.*, 19, 1857 (1971); G. R. Newkome and S. J. Garbis, *J. Heterocyclic Chem.*, 15, 685 (1978); W. Roszkiewicz and M. Wozniak, Synthesis, 691–692 (1976); *J. Heterocyclic Chem*, Vol. 9, 703–706 (1972); *Polish Journal of Chemistry*, 52, 2369–2376, (1978); *Chemical Pharm. Bull.*, Vol. 17 (5), 1045–1050, (1969); *J. Org. Chem*, Vol. 36, No. 3, 450–454 (1971); *Tetrahedron Letters*, No. 12, 1233–1237, (1966); *J. Org. Chem.*, Vol. 37, No. 20, 3101–3105 (1972); U.S. Pat. No. 4,308,273 (preparation of 1,6-naphthyridine); *CA* 111959, Vol. 82, 503 (1975); *J.A.C.S.*, Vol. 77, 2438–2440, (1955); and E. M. Hawes and D. G. Wibberley, *J. Chem. Soc., C.*, 1564–1568 (1967); all of which are incorporated herein by reference and made a part hereof. The 2-(4-hydroxy (or mercapto)phenoxy)-propanoic acid and derivatives thereof employed as starting materials are known compounds.

What is claimed is:

1. A compound of the formula

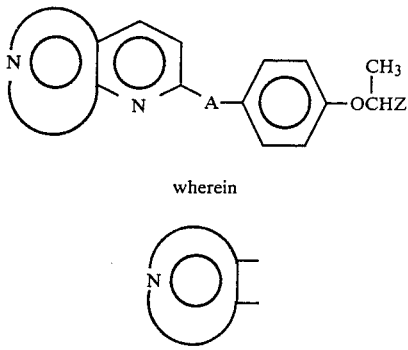

wherein represents a fused six-membered nitrogen-containing aromatic ring which forms a 1,5-, 1,6-, 1,7- or 1,8-naphthyridinyl moiety with the adjoining pyridine ring, said naphthyridinyl moiety optionally being substituted at the 6-position of the naphthyridinyl moiety with a chloro, iodo, $CF_3$, bromo, or fluoro atom with the proviso that said substitution occurs only when the 6-position of said naphthyridinyl moiety is occupied by a carbon atom;

A represents O or S;

Z represents —$CONR'_2$ or —$CSNH_2$; and

R' represents H or $C_1$–$C_4$ alkyl.

2. The compound of claim 1 wherein said naphthyridinyl moiety is substituted at the 6-position with a chloro atom.

3. The compound of claim 1 which is an agriculturally acceptable amide of 2-(4-((6-chloro-2-(1,5-naphthyridinyl))oxy)phenoxy)propanoic acid.

4. The compound of claim 1 which is an agriculturally acceptable amide of 2-(4-((6-chloro-2-(1,7-naphthyridinyl))oxy)phenoxy)propanoic acid.

5. The compound of claim 1 which is an agriculturally acceptable amide of 2-(4-(2-(1,8-naphthyridinyl)oxy)phenoxy)propanoic acid.

6. The compound of claim 1 which is an agriculturally acceptable amide of 2-(4-(2-(1,6-naphthyridinyl)oxy)phenoxy)propanoic acid.

7. The compound of claim 1 wherein said naphthyridinyl moiety is a 1,5-naphthyridinyl moiety.

8. The compound of claim 1 wherein said naphthyridinyl moiety is a 1,6-naphthyridinyl moiety.

9. The compound of claim 1 wherein said naphthyridinyl moiety is a 1,7-naphthyridinyl moiety.

10. The compound of claim 1 wherein said naphthyridinyl moiety is a 1,8-naphthyridinyl moiety.

11. A composition comprising an inert agricultural carrier and a herbicidally effective amount of an active compound of the formula

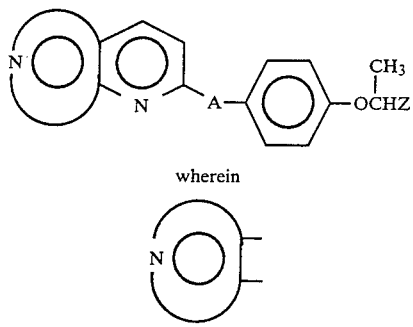

wherein represents a fused six-membered nitrogen-containing aromatic ring which forms a 1,5-, 1,6-, 1,7- or 1,8-naphthyridinyl moiety with the adjoining pyridine ring, said naphthyridinyl moiety optionally being substituted at the 6-position of the naphthyridinyl moiety with a chloro, iodo, $CF_3$, bromo, or fluoro atom with the proviso that said substitution occurs only when the 6-position of said naphthyridinyl moiety is occupied by a carbon atom;

A represents O or S;

Z represents —$CONR'_2$ or —$CSNH_2$; and

R' represents H or $C_1$–$C_4$ alkyl.

12. The composition of claim 11 wherein said active compound is an agriculturally acceptable amide of 2-(4-((6-chloro-2-(1,5-naphthyridinyl))oxy)phenoxy)-propanoic acid.

13. The composition of claim 12 wherein said active compound is present in the range of from about 0.003 to about 95 percent by weight of the total composition.

14. A method of controlling undesired plant growth which comprises applying to the locus of said plants a herbicidally effective amount of an active compound of the formula

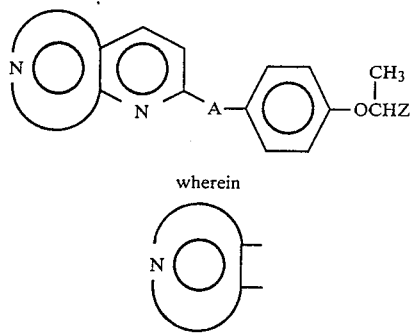

wherein represents a fused six-membered nitrogen-containing aromatic ring which forms a 1,5-, 1,6-, 1,7- or 1,8-naphthyridinyl moiety with the adjoining pyridine ring, said naphthyridinyl moiety optionally being substituted at the 6-position of the naphthyridinyl moiety with a chloro, iodo, $CF_3$, bromo, or fluoro atom with the proviso that said substitution occurs only when the 6-position of said naphthyridinyl moiety is occupied by a carbon atom;

A represents O or S;

Z represents —$CONR'_2$ or —$CSNH_2$; and

R' represents H or $C_1$–$C_4$ alkyl.

15. The method of claim 14 wherein said active compound is an agriculturally acceptable amide of 2-(4-((6-chloro-2-(1,5-naphthyridinyl))oxy)phenoxy)propanoic acid.

16. The method of claim 15 wherein said active compound applied in an amount in the range of from about 0.01 to about 20 lbs/acre.

17. The method of claim 16 wherein said active compound is applied in preemergent operations in an amount of from about 0.05 to about 4 lbs/acre.

* * * * *